United States Patent [19]
Goto et al.

[11] Patent Number: 5,677,156
[45] Date of Patent: Oct. 14, 1997

[54] METHOD FOR PRODUCING FUMARIC ACID

[75] Inventors: Makoto Goto; Izuru Tokumaru; Masato Terasawa; Hideaki Yukawa, all of Inashiki-gun, Japan

[73] Assignee: Mitsubishi Chemical Corporation, Tokyo, Japan

[21] Appl. No.: 623,001

[22] Filed: Mar. 28, 1996

[30] Foreign Application Priority Data

Apr. 4, 1995 [JP] Japan ................... 7-102976

[51] Int. Cl.$^6$ ................ C12P 7/46; C12N 9/90
[52] U.S. Cl. ............ 435/145; 435/109; 435/233; 435/829; 435/840
[58] Field of Search ................ 435/145, 233

[56] References Cited

U.S. PATENT DOCUMENTS

| | | | |
|---|---|---|---|
| 2,332,992 | 10/1943 | Davis | 51/263 |
| 2,816,923 | 12/1957 | Stephenson | 260/537 |
| 2,955,136 | 10/1960 | Sullivan et al. | 260/537 |
| 4,877,731 | 10/1989 | Ling et al. | 435/145 |

OTHER PUBLICATIONS

Ken'ichi Otsuka, "Isomerisation from Maleic Acid to Fumaric Acid", Agr. Biol. Chem., vol. 25, No. 9, pp. 726–730, 1961.

*Primary Examiner*—Herbert J. Lilling
*Attorney, Agent, or Firm*—Wenderoth, Lind & Ponack

[57] ABSTRACT

Fumaric acid is produced by reacting maleic acid in an aqueous solution with a microorganism which has maleate isomerase activity or with a preparation from the microorganism having the maleate isomerase activity, and producing fumaric acid in a reaction solution by enzymatic isomerization of maleic acid carried out under the condition that the dissolved oxygen concentration in the reaction solution is substantially maintained at 4 ppm or less, for example, by sealing the reaction solution with one or more gases selected from $N_2$, Ar, and He.

10 Claims, No Drawings

METHOD FOR PRODUCING FUMARIC ACID

BACKGROUND OF THE INVENTION

1. Field of the Invention

The present invention relates to a method for efficiently producing fumaric acid from maleic acid. Fumaric acid is principally produced by isomerization of maleic acid, and it is widely used in the production of pharmaceuticals, food, and industrial raw materials. For example, L-aspartic acid, L-malic acid, and L-alanine, which are useful for food, pharmaceuticals, and industrial raw materials, are produced from fumaric acid by means of enzymatic methods or other methods.

2. Description of Related Art

Chemical methods have been principally proposed as methods for producing fumaric acid by isomerizing maleic acid (U.S. Pat. Nos. 2,816,923; 2,955,136, and 2,332,992). However, these methods involve, for example, the following problems. Firstly, the ratio of conversion into fumaric acid is restricted by reaction equilibrium. Secondly, maleic acid or fumaric acid is degraded because these methods involve a reaction at a high temperature. Finally, the yield is decreased due to generation of by-products.

On the other hand, an enzymatic method is also known, in which maleate isomerase isomerizes maleic acid to fumaric acid (K. Otsuka, Agric. Biol. Chem., 25, (9), p. 726 (1961)). However, such a document merely describes investigation on enzymatic properties, in which little investigation has been made from the viewpoint of industrial application.

SUMMARY OF THE INVENTION

The present invention has been made taking into account the above considerations. One object of the invention is to provide a practical method which makes it possible to produce fumaric acid from maleic acid efficiently at a high yield in accordance with an enzymatic process.

As a result of diligent investigations by the present inventors in order to establish a method for efficiently producing fumaric acid, it has been found that fumaric acid can be produced at a high yield by reacting maleic acid in an aqueous solution with a microorganism which has maleate isomerase activity or with a preparation from the microorganism which has the maleate isomerase activity, and producing fumaric acid from maleic acid by the enzymatic isomerization, wherein the enzymatic reaction is carried out under the condition that a dissolved oxygen concentration in a reaction solution is substantially maintained at 4 ppm or less. Thus the present invention has been completed.

The present invention will be explained in detail below.

All of the microorganism which have maleate isomerase activity can be used in the present invention. However, those preferably used include microorganisms belonging to the genera Alcaligenes, Pseudomonas, Xanthomanas, and Bacillus. Especially, those preferably used include, for example, *Alcaligenes faecalis* (for example, IFO 12669, IFO 13111, and IAM 1473), *Alcaligenes eutrophus*, *Pseudomonas fluolescens* (for example, ATCC 23728), *Xanthomonas maltophilia* (for example, ATCC 13270), *Bacillus stearothermophilus* (for example, MI-101 strain (FERM P-14802)), and *Bacillus brevis* (for example, MI-103 strain (FERM P-14803)). No problem occurs even in the case of the use of, for example, a mutant strain or a genetically recombined modified strain obtained from the microorganisms described above, or a microorganism which is improved by introducing a maleate isomerase gene obtained from any one of the microorganisms described above into another microorganism.

The microorganism which has maleate isomerase activity can be cultivated in an ordinary nutrient medium containing a carbon source, a nitrogen source, inorganic salts, various vitamins, and so on. Those used as the carbon source include, for example, maleic acid; sugar such as glucose, sucrose, fructose, and maltose; alcohol such as ethanol and methanol; organic acid such as acetic acid, citric acid and malic acid; and molasses. Preferably, glucose, acetic acid and ethanol is used as the carbon source. Those used as the nitrogen source include, for example, ammonia, ammonium sulfate, ammonium chloride, ammonium nitrate, and urea. These nitrogen sources are used singly or in a mixture respectively. Those used as the inorganic salts include, for example, dipotassium hydrogenphosphate, potassium dihydrogenphosphate, and magnesium sulfate. Other than the above, the medium can be supplemented with nutrients including, for example, peptone, meat extract, yeast extract, corn steep liquor, casamino acid, and various vitamins such as biotin. Further, the medium may be supplemented with an inducing substance for maleate isomerase, such as maleic acid, malonic acid, tartronic acid, citraconic acid, and mesaconic acid. The inducing substance is added usually at a concentration of 10 to 200 mM, preferably 50 to 100 mM.

The cultivation condition is not specifically limited provided that the microorganism which has the maleate isomerase activity is cultivated at a temperature which allows its growth usually under an aerobic condition with aeration, agitation, shaking or the like. There is also no special limitation for pH during the cultivation provided that the microorganism is cultivated at a pH which allows its growth. It is possible to adjust pH during the cultivation by adding acid or alkali.

A culture is thus obtained, from which microbial cells are recovered, for example, by centrifugation. Thus microbial cells which contains maleate isomerase can be obtained.

In the present invention, the isomerization reaction from maleic acid to fumaric acid can be of course carried out by using the microbial cells recovered from a culture liquid obtained by cultivating the microorganism described above. The isomerization reaction can be also carried out by using the preparation such as a culture liquid, disrupted microbial cells, or an extract from microbial cells. The microbial cells may be used after washing with a buffer such as a phosphate buffer (pH 7). Alternatively, a crude enzyme sample obtained from the microbial cells may be used, or a purified enzyme sample may be used. It is also possible to use the immobilized preparation of the microbial cells, the disrupted microbial cells, the extract from microbial cells, or the purified enzyme. The "preparation from a microorganism which has a maleate isomerase activity" referred to herein includes all fractions as those described above originating from the microbial cells and having the maleate isomerase activity. In the case of the use of the microbial cells, the permeability of the microbial cells can be enhanced before the use by previously freezing the microbial cells, or by treating the microbial cells at a temperature of 15° to 40° C. for 10 to 120 minutes in a solution prepared by adding a surfactant (0.01 to 0.2%) such as Triton X-100 and Tween 20 to the buffer described above.

In the present invention, the process of "reacting maleic acid in an aqueous solution with a microorganism which has a maleate isomerase activity or with a preparation from the microorganism which has the maleate isomerase activity"

includes a process to add maleic acid or an aqueous solution which contains maleic acid to the microbial cells, the preparation therefrom, or an aqueous solution which contains any one or both of them, and a process to allow an aqueous solution which contains maleic acid to pass through a column charged with the immobilized microbial cells, the immobilized disrupted cells or the immobilized enzyme.

Any one of known methods for enzyme purification can be applied to the method for extracting and purifying maleate isomerase from the microbial cells. Usable methods for disrupting the microbial cells include, for example, mechanical disrupting methods by using a ultrasonic disrupter, a French press, a homogenizer or the like, and enzymatic disrupting methods by using lysozyme or the like. A soluble fraction of disrupted cells thus obtained or its fractionated sample thereof can be used as a crude enzyme solution of maleate isomerase. Alternatively, it is allowable to use purified enzyme obtained by further purification of the crude enzyme fraction. Purification of maleate isomerase from the crude enzyme fraction can be usually carried out by using methods of (a) separation by precipitation such as ammonium sulfate precipitation, (b) separation by chromatography such as ion exchange chromatography, affinity adsorption chromatography, and gel filtration chromatography, and (c) separation by electrophoresis, or by using an arbitrary combination of these methods.

The present invention comprises the steps of reacting an aqueous solution containing maleic acid with a microorganism which has a maleate isomerase activity or with a preparation therefrom, and producing fumaric acid from maleic acid by the enzymatic isomerization, characterized in that the reaction is carried out under the condition that the dissolved oxygen concentration in a reaction solution is substantially maintained at not more than 4 ppm, preferably at not more than 0.5 ppm.

However, it is sufficient for the dissolved oxygen level to be maintained substantially at 4 ppm or less for a long period of time even if the dissolved oxygen level temporarily exceeds 4 ppm. For example, if the dissolved oxygen level temporarily exceeds 4 ppm immediately after starting agitation or immediately after preparing a maleic acid-containing aqueous solution, it is allowable for the dissolved oxygen level to be maintained at 4 ppm or less thereafter. If the dissolved oxygen level exceeds 4 ppm for a certain short period of time, for example, due to increase the degree of rotational agitation during the reaction, it is allowable for the dissolved oxygen level to be maintained at 4 ppm or less for an almost all period of entire reaction time.

A method for maintaining the dissolved oxygen concentration at 4 ppm or less in the reaction solution specifically includes, for example, sealing of the reaction solution with one or more gases selected from $N_2$, Ar, and He; addition of a sulfite to the reaction solution or a material thereof; and deaeration of the reaction solution or a material thereof. These methods may be used in combination.

The "one or more gases selected from $N_2$, Ar, and He" refer to the respective single gases, or an arbitrary combination of the two or more gases. A method for performing the maleate isomerase reaction in an atmosphere formed by these gases includes, for example, the following methods. Namely, (a) the gas or gasses are continuously blown in a maleic acid aqueous solution or an enzyme reaction solution (hereinafter simply referred to as "reaction solution") during the enzyme reaction and/or before the enzyme reaction, (b) the gas or gases are blown in the reaction solution followed by tight sealing, and (c) the gas or gases are introduced into a reaction vessel containing the reaction solution which has been deaerated and then tightly sealed. It is sufficient for the method of the present invention that a gas phase contacting with the reaction solution is in an atmosphere of the gas or gases, namely the reaction solution is sealed with the gas or gases. It is not necessarily indispensable that the gas or gases should be continuously blown in the reaction solution or in the reaction vessel. Preferably, the gas phase contacting with the reaction solution is completely substituted with the gas or gases. However, it is possible to expect an effect of substitution even in the case of partial substitution of the gas phase.

The sulfite used in the present invention may be any salt of sulfurous acid. It is preferable to use inorganic sulfites such as sodium sulfite, potassium sulfite, ammonium sulfite, ammonium hydrogensulfite, and calcium sulfite. However, it is inadequate to use salts of mercury and copper which are known to inhibit the maleate isomerase activity concerning the present invention. The sulfite is used at a concentration of 1 ppm to 1,000 ppm, preferably 10 ppm to 500 ppm.

A method for decreasing the dissolved oxygen concentration of the reaction solution or the material thereof by deaeration is not specifically limited. For example, it is possible to adopt a method of heating the reaction solution to a temperature of about 55° C. under a reduced pressure achieved by using an aspirator, and a method of expelling air in the solution under a reduced pressure while giving vibration by using a ultrasonic. As for the deaeration, the material of the reaction solution, for example, a maleic acid aqueous solution or an aqueous solution containing the microbial cells or the preparation therefrom may be deaerated before the reaction. Alternatively, the reaction solution may be deaerated during the reaction.

The enzyme reaction is carried out usually for 5 to 120 hours at a pH of 5 to 10, preferably 6 to 9 and at a temperature of 20° to 50° C., preferably 25° to 37° C. The reaction solution may be added with salts of divalent metals such as salts of calcium, magnesium, and manganese, if necessary. The reaction solution may further contain a buffering agent, a minute amount of organic solvent, and so on.

The aqueous solution containing maleic acid used for the reaction has a maleic acid concentration of 1 to 40 W/V %, preferably 10 to 30 W/V %. However, the maleic acid concentration is occasionally maintained at about 0.001 to 1%, for example, in a continuous reaction.

The amount of addition of the microbial cells or the preparation therefrom used for the reaction is not specifically limited. However, the microbial cells are preferably used in 1 to 30% in weight (as wet microbial cells).

Fumaric acid produced by the method described above is separated from the microbial cells and the preparation therefrom, for example, by separation with a ultrafiltration membrane or by centrifugation. After that, fumaric acid is precipitated by a known method such as isoelectric precipitation with sulfuric acid, followed by washing with water and drying. Thus fumaric acid can be collected as crystals.

In an additional aspect of the present invention, the produced fumaric acid can be used to produce L-aspartic acid by the action of cells of an aspartase-containing microorganism such as *Brevibacterium flavum* AB-41 strain (FERM BP-1498) and *Eschirichia coli* ATCC 11303. Alternatively, L-aspartic acid can be efficiently produced from maleic acid by adding the aspartase-containing microorganism to the reaction system of the present invention to perform the reaction.

In another additional aspect of the present invention, the produced fumaric acid can be used to produce L-malic acid by the action of cells of a fumarase-containing microorganism such as *Brevibacterium flavum* AB-41 strain (FERM BP-1498) and *E. coli* ATCC 11303. Alternatively, L-malic acid can be efficiently produced from maleic acid by adding the fumarase-containing microorganism to the reaction system of the present invention to carry out the reaction.

According to the method of the present invention, fumaric acid can be produced from maleic acid efficiently at a high yield in accordance with the enzymatic process.

In the present invention, the phrase "producing fumaric acid from maleic acid" does not necessarily mean accumulation of fumaric acid. The phrase means the conversion of maleic acid to fumaric acid, as exemplified by the production of L-aspartic acid and L-malic acid from maleic acid via fumaric acid as described above.

DESCRIPTION OF PREFERRED EMBODIMENTS

The present invention will be more specifically explained with reference to the following Examples.

EXAMPLE 1

Production of Fumaric Acid in $N_2$ Atmosphere (1) Cultivation of microorganism which has maleate isomerase activity A medium (100 ml) having a composition comprising meat extract (10 g), peptone (10 g), NaCl (5 g), maleic acid (10 g), and distilled water (1,000 ml) (with pH adjusted to 7.0 with sodium hydroxide) was dispensed and poured into an Erlenmeyer flask having a volume of 500 ml, and sterilized by a treatment at 120° C. for 20 minutes, which was inoculated with *Alcaligenes faecalis* IFO 12669 strain to carry out cultivation with shaking at 30° C. for 24 hours.

The medium (1,000 ml) of the same composition as that described above was introduced into a jar fermenter having a volume of 3 L, and sterilized by a treatment at 120° C. for 20 minutes, which was inoculated with a culture liquid (30 ml) obtained by the above mentioned procedure, to carry out further cultivation at 30° C. for 24 hours. An obtained culture liquid was centrifuged (8,000 rpm, 15 minutes, 4° C.) to recover microbial cells which were washed once with 0.1M phosphate buffer (pH 7.0), and subjected to the following reaction.

(2) Production of fumaric acid from maleic acid

A reaction solution containing maleic acid (116 g) and 5N sodium hydroxide (400 ml) (having a total volume of 1,000 ml by adding water), which had been previously subjected to $N_2$ substitution by carrying out agitation while blowing $N_2$ gas in it for 30 minutes, was transferred into a jar fermenter having a volume of 3 L. The recovered microbial cells (IFO 12669 strain, 20 g) were added thereto, followed by agitation while supplying $N_2$ to the gas phase at a velocity of 0.02 vvm to carry out a reaction at 30° C. for 36 hours. During the reaction, the dissolved oxygen concentration was maintained at 0.5 ppm or less. After completion of the reaction, a supernatant was recovered by centrifugation. The obtained supernatant of the reaction solution was subjected to high performance liquid chromatography analysis (LC-5A, produced by Shimadzu) by using a column for organic acid analysis (SCR-101H column, produced by Shimadzu) and a UV detector (at a wavelength of 210 nm). As a result, it was confirmed that 66 g/L of fumaric acid was produced. Fumaric acid was quantitatively determined by using pimelic acid as an internal standard substance. After the analysis for the supernatant of the reaction solution described above, fumaric acid was precipitated by lowering pH to 3 with sulfuric acid. Obtained crystals of fumaric acid had an amount of 63 g.

EXAMPLE 2

Production of Fumaric Acid in Ar Atmosphere (1) Cultivation of microorganism which has maleate isomerase activity

*Alcaligenes faecalis* IFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water), which had been previously subjected to Ar substitution by carrying out agitation while blowing Ar gas in it for 30 minutes, was transferred into a jar fermenter having a volume of 3 L. The recovered microbial cells (IFO 12669 strain, 20 g) were added thereto, followed by agitation while supplying Ar to the gas phase at a velocity of 0.02 vvm to carry out a reaction at 30° C. for 36 hours with sealing. During the reaction, the dissolved oxygen concentration was maintained at 0.5 ppm or less. Fumaric acid was obtained in an amount of 65 g/L. Crystals of fumaric acid were obtained in the same manner as in Example 1. The obtained crystals had an amount of 62.5 g.

EXAMPLE 3

Production of Fumaric Acid in He Atmosphere (1) Cultivation of microorganism which has maleate isomerase activity

*Alcaligenes faecalis* IFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water), which had been previously subjected to He substitution by carrying out agitation while blowing He gas in it for 30 minutes, was transferred into a jar fermenter having a volume of 3 L. The recovered microbial cells (IFO 12669 strain, 20 g) were added thereto, followed by agitation while supplying He to the gas phase at a velocity of 0.02 vvm to carry out a reaction at 30° C. for 36 hours with sealing. During the reaction, the dissolved oxygen concentration was maintained at 0.5 ppm or less. Fumaric acid was obtained in an amount of 67 g/L. Crystals of fumaric acid were obtained in the same manner as in Example 1. The obtained crystals had an amount of 63.5 g.

EXAMPLE 4

Production of Fumaric Acid in $N_2$-Substituted Reaction Solution (1) Cultivation of microorganism which has maleate isomerase activity

*Alcaligenes faecalis* IFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water), which had been previously subjected to $N_2$ substitution by carrying out agitation while blowing $N_2$ gas in it for 30 minutes, was transferred into a jar fermenter having a volume of 3 L. The microbial cells (IFO 12669 strain, 20 g) recovered in Example 1 were added thereto, followed by agitation to carry out a reaction at 30° C. for 36 hours. During the reaction, the dissolved oxygen concentration was maintained at about 4 ppm or less. Fumaric acid was obtained in an amount of 52.4 g/L. Fumaric acid was precipitated by lowering pH to 3 with sulfuric acid after centrifugation in accordance with an ordinary method. Obtained crystals of fumaric acid had an amount of 49.2 g.

EXAMPLE 5

Production of Fumaric Acid in Reaction Solution Added with Sodium Sulfite (1) Cultivation of microorganism which has maleate isomerase activity

*Alcaligenes faecalis* IFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water) was added with 0.2 g/L of sodium sulfite, and transferred into a jar fermenter having a volume of 3 L. The microbial cells (IFO 12669 strain, 20 g) recovered in Example 1 were added thereto. The jar was tightly sealed and agitated to carry out a reaction at 30° C. for 36 hours. During the reaction, the dissolved oxygen concentration was maintained at about 3 ppm or less. Fumaric acid was obtained in an amount of 54.5 g/L. Fumaric acid was precipitated by lowering pH to 3 with sulfuric acid after centrifugation in accordance with an ordinary method. Obtained crystals of fumaric acid had an amount of 51 g.

EXAMPLE 6

Production of Fumaric Acid in Deaerated Reaction Solution (1) Cultivation of microorganism which has maleate isomerase activity Alcaligenes faecalisIFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water) was introduced into a pressure bottle, and deaerated for 15 minutes while carrying out evaporation by using a water-jet aspirator. After the pressure was calmly returned to the atmospheric pressure, the reaction solution was transferred into a jar fermenter having a volume of 3 L. The microbial cells (*Alcaligenes faecalis* IFO 12669 microbial strain, 20 g) recovered in Example 1 were added thereto. The jar was tightly sealed and agitated to carry out a reaction at 30° C. for 36 hours. During the reaction, the dissolved oxygen concentration was maintained at about 4 ppm or less. Fumaric acid was obtained in an amount of 51.3 g/L. Fumaric acid was precipitated by lowering pH to 3 with sulfuric acid after centrifugation in accordance with an ordinary method. Obtained crystals of fumaric acid had an amount of 48 g.

CONTROL EXAMPLE

Production of Fumaric Acid in Atmospheric Air (1) Cultivation of microorganism which has maleate isomerase activity

*Alcaligenes faecalis* IFO 12669 strain was cultivated in the same manner as in Example 1.

(2) Production of fumaric acid from maleic acid

A reaction solution containing maleic acid (116 g) and 5N sodium hydroxide (400 ml) (having a total volume of 1,000 ml by adding water), which had not been subjected to blowing with $N_2$, was transferred into a jar fermenter having a volume of 3 L. The recovered microbial cells (IFO 12669 strain, 20 g) were added thereto, followed by agitation without $N_2$ sealing to carry out a reaction at 30° C. for 36 hours. Fumaric acid was obtained in an amount of 44 g/L. Crystals of fumaric acid were obtained in the same manner as in Example 1. The obtained crystals had an amount of 41 g.

REFERENCE EXAMPLE 1

Production of Aspartic Acid (1) Cultivation of microorganism which has maleate isomerase activity

*Alcaligenes faecalis* IFO 12669 strain was cultivated in the same manner as in Example 1.

(2) Cultivation of microorganism which has ability to produce aspartic acid from fumaric acid A medium (100 ml) having a composition comprising urea (4 g), $(NH_4)_2SO_4$ (14 g), $KH_2PO_4$ (0.5 g), $K_2HPO_4$ (0.5 g), $MgSO_4.7H_2O$ (0.5 g), $FeSO_4.7H_2O$ (20 mg), $MnSO_4.nH_2O$ (20 mg), D-biotin (200 µg), thiamine hydrochloride (100 µg), yeast extract (1 g), casamino acid (1 g), and distilled water (1,000 ml, pH 6.6) was dispensed and poured into an Erlenmeyer flask having a volume of 500 ml, and sterilized by a treatment at 120° C. for 15 minutes. The medium was added with a sterilized 50% glucose aqueous solution (4 ml), and inoculated with *Brevibacterium flavum* AB-41 strain (FERM BP-1498) to carry out cultivation with shaking at 33° C. for 24 hours.

The medium (1,000 ml) of the same composition as that described above was poured into a jar fermenter having a volume of 2 L, and sterilized by a treatment at 120° C. for 20 minutes, which was added with a culture liquid (20 ml) obtained by the above mentioned procedure and a sterilized 50% glucose aqueous solution (200 ml) to carry out further cultivation at 33° C. for 24 hours. An obtained culture liquid was centrifuged (8,000 rpm, 15 minutes, 4° C.) to recover microbial cells. A contaminating activity of by-producing malic acid was removed from the recovered microbial cells in accordance with the following method. Namely, the recovered microbial cells were suspended in a solution having a composition comprising aspartic acid (100 g), ammonia (180 ml), calcium chloride (2.2 g), and Tween 20 (0.8 g) (having a total volume of 1 L by adding water), and shaken at 45° C. for 3 hours. The microbial cells were recovered by centrifugation (8,000 rpm, 15 minutes, 4° C.).

(3) Production of aspartic acid from maleic acid and ammonia

A reaction solution containing maleic acid (116 g) and ammonia (153 ml) (having a total volume of 1,000 ml by adding water), which had been previously subjected to $N_2$ substitution by carrying out agitation while blowing $N_2$ gas in it for 30 minutes, was transferred into a jar fermenter having a volume of 3 L. The recovered microbial cells of the both species (IFO 12669 strain: 20 g, AB-41 strain: 120 g) were added thereto, followed by agitation while supplying $N_2$ at a velocity of 0.02 vvm to carry out a reaction at 30° C. for 36 hours with sealing. After completion of the reaction, a supernatant was recovered by centrifugation. The obtained supernatant of the reaction solution was subjected to thin layer chromatography (developing solvent: n-butanol: acetic acid: water=4:1:1 (volume ratio), coloring agent: ninhydrin reagent). As a result, it was confirmed that 128 g/L of L-aspartic acid was produced. Sulfuric acid was added to this ammonium aspartate solution to adjust pH to 3. Thus aspartic acid was precipitated, washed with water, and then dried to obtain crystals of aspartic acid. The obtained crystals had an amount of 125 g.

REFERENCE EXAMPLE 2

Production of L-Malic Acid (1) Cultivation of microorganism which has maleate isomerase activity

*Alcaligenes faecalis* IFO 12669 strain was cultivated in the same manner as in Example 1.

(2) Cultivation of microorganism which has ability to produce L-malic acid from fumaric acid A medium (100 ml) having a composition comprising urea (4 g), $(NH_4)_2SO_4$ (14 g), $KH_2PO_4$ (0.5 g), $K_2HPO_4$ (0.5 g), $MgSO_4 \cdot 7H_2O$ (0.5 g), $FeSO_4 \cdot 7H_2O$ (20 mg), $MnSO_4 \cdot nH_2O$ (20 mg), D-biotin (200 µg), thiamine hydrochloride (100 µg), yeast extract (1 g), casamino acid (1 g), and distilled water (1,000 ml, pH 6.6) was dispensed and poured into an Erlenmeyer flask having a volume of 500 ml, and sterilized by a treatment at 120° C. for 15 minutes. The medium was added with a sterilized 50% glucose aqueous solution (4 ml), and inoculated with *Brevibacterium flavum* AB-41 microbial strain (FERM BP-1498) to carry out cultivation with shaking at 33° C. for 24 hours.

The medium (1,000 ml) of the same composition as that described above was poured into a jar fermenter having a volume of 2 L, and sterilized by a treatment at 120° C. for 20 minutes, which was added with a culture liquid (20 ml) obtained by the above mentioned procedure and a sterilized 50% glucose aqueous solution (200 ml) to carry out further cultivation at 33° C. for 24 hours. An obtained culture liquid was centrifuged (8,000 rpm, 15 minutes, 4° C.) to recover microbial cells. A contaminating fumarase and an activity of by-producing succinic acid were removed from the microbial cells in accordance with the following method. Namely, the recovered microbial cells were suspended in a solution having a composition comprising disodium fumarate (32 g) and Tween 20 (0.8 g) (having a total volume of 1 L by adding water), and shaken at 45° C. for 3 hours. The microbial cells were recovered by centrifugation (8,000 rpm, 15 minutes, 4° C.).

(3) Production of L-malic acid from maleic acid

A reaction solution containing maleic acid (116 g) and 5N sodium hydroxide (200 ml) (having a total volume of 1,000 ml by adding water), which had been previously subjected to $N_2$ substitution by carrying out agitation while blowing $N_2$ gas in it for 30 minutes, was transferred into a jar fermenter having a volume of 3 L. The microbial cells of the both species (IFO 12669 strain: 20 g, AB-41 strain: 50 g), which had been recovered in Example 1 and in the item (1) described above, were added thereto, followed by agitation while supplying $N_2$ at a velocity of 0.02 vvm to carry out a reaction at 30° C. for 36 hours with sealing. L-Malic acid was obtained in an amount of 104 g/L. Calcium chloride was added to the obtained solution of sodium L-malate to precipitate calcium malate, followed by washing with water. After that, L-malic acid was separated by using an ion exchange resin, and dried. Thus crystals of L-malic acid were obtained. The obtained crystals had an amount of 90 g.

What is claimed is:

1. A method for producing fumaric acid comprising the steps of:

reacting maleic acid in an aqueous solution with a microorganism which has a maleate isomerase activity or with a preparation from the microorganism having the maleate isomerase activity to obtain a reaction solution, and producing fumaric acid from maleic acid by enzymatic isomerization, wherein the reaction is carried out under a condition that the reaction solution has a dissolved oxygen concentration which is substantially maintained at 4 ppm or less.

2. A method for producing fumaric acid according to claim 1, wherein the dissolved oxygen concentration in the reaction solution is substantially maintained at 4 ppm or less by sealing the reaction solution with one or more gases selected from $N_2$, Ar, and He.

3. A method for producing fumaric acid according to claim 1, wherein the dissolved oxygen concentration in the reaction solution is substantially maintained at 4 ppm or less by adding a sulfite to the reaction solution or to a material which forms the reaction solution.

4. A method for producing fumaric acid according to claim 1, wherein the dissolved oxygen concentration in the aqueous solution containing maleic acid is substantially maintained at 4 ppm or less by deaerating the reaction solution or a material which forms the reaction solution.

5. A method for producing fumaric acid according to claim 1, wherein the dissolved oxygen concentration in the reaction solution is maintained at 0.5 ppm or less.

6. A method for producing fumaric acid according to claim 2, wherein the dissolved oxygen concentration in the reaction solution is maintained at 0.5 ppm or less.

7. A method for producing fumaric acid according to claim 3, wherein the dissolved oxygen concentration in the reaction solution is maintained at 0.5 ppm or less.

8. A method for producing fumaric acid according to claim 4, wherein the dissolved oxygen concentration in the reaction solution is maintained at 0.5 ppm or less.

9. A method for producing fumaric acid according to claim 3, wherein the material is a maleic acid aqueous solution or an aqueous solution containing cells of the microorganism or the preparation from the microorganism.

10. A method for producing fumaric acid according to claim 4, wherein the material is a maleic acid aqueous solution or an aqueous solution containing cells of the microorganism or the preparation from the microorganism.

* * * * *